United States Patent
Faubert et al.

(10) Patent No.: US 10,743,807 B2
(45) Date of Patent: Aug. 18, 2020

(54) SYSTEM AND METHOD FOR DETERMINING A PERCEPTUAL-COGNITIVE SIGNATURE OF A SUBJECT

(71) Applicant: Cognisens Inc., Montrèal, Quèbec (CA)

(72) Inventors: Jocelyn Faubert, Montrèal (CA); Jean Castonguay, Vaudreuil-Dorion (CA); Lee Sidebottom, Stalybridge (GB); Brendan Parsons, Montrèal (CA)

(73) Assignee: COGNISENS INC., Montreal, Quebec (CA)

( * ) Notice: Subject to any disclaimer, the term of this patent is extended or adjusted under 35 U.S.C. 154(b) by 571 days.

(21) Appl. No.: 15/105,621

(22) PCT Filed: Dec. 19, 2014

(86) PCT No.: PCT/CA2014/051240
§ 371 (c)(1),
(2) Date: Jun. 17, 2016

(87) PCT Pub. No.: WO2015/089673
PCT Pub. Date: Jun. 25, 2015

(65) Prior Publication Data
US 2016/0310059 A1    Oct. 27, 2016

Related U.S. Application Data

(60) Provisional application No. 61/918,549, filed on Dec. 19, 2013.

(51) Int. Cl.
*A61B 5/16* (2006.01)
*A61B 5/00* (2006.01)

(52) U.S. Cl.
CPC ............ *A61B 5/168* (2013.01); *A61B 5/4088* (2013.01); *A61B 5/7271* (2013.01); *A61B 5/7445* (2013.01); *A61B 5/162* (2013.01)

(58) Field of Classification Search
CPC ......... A61B 5/16; A61B 5/168; A61B 5/4088; A61B 5/68; A61B 5/7271
See application file for complete search history.

(56) References Cited

U.S. PATENT DOCUMENTS

| 5,911,581 A | 6/1999 | Reynolds et al. |
| 2011/0005532 A1 | 1/2011 | Faubert et al. |

FOREIGN PATENT DOCUMENTS

| CA | 2774257 | 4/2010 |
| WO | WO 2010/037222 A1 | 4/2010 |
| WO | WO 2014/146192 A1 | 9/2014 |

OTHER PUBLICATIONS

Beauchamp, et al., "Visual Perception Training: Cutting Edge Psychophysics and 3D Technology Applied to Sport Science", In Press 2011.

(Continued)

*Primary Examiner* — Patrick Fernandes
(74) *Attorney, Agent, or Firm* — Praxis

(57) ABSTRACT

The present disclosure relates to a system and a method for determining a perceptual-cognitive signature of a subject. A plurality of objects moves at a controlled speed on a visual display, for a predetermined duration in each of a series of core trials. The subject identifies one or more target objects amongst the plurality of objects. The perceptual-cognitive signature of the subject is determined according to the number of target objects, the speed of the objects, the predetermined duration of each of the series of core trials, and a correctness of identifications, by the subject after each predetermined duration, of the target objects over the series of core trials.

13 Claims, 14 Drawing Sheets

(56) References Cited

OTHER PUBLICATIONS

Faubert, et al., "Perceptual-Cognitive Training of Athletes", Journal of Clinical Sport Psychology, 2012, 6, 85-102, Human Kinetics, Inc.
Lugo, et al., "Multisensory Integration Central Processing Modifies Peripheral Systems," Psychological Science, vol. 19, No. 10, 2008.
Lugo, et al., "Ubiquitous Crossmodal Stochastic Resonance in Humans: Auditory Noise Facilitates Tactile, Visual and Proprioceptive Sensations," PLoS ONE, Aug. 2008, vol. 3, Issue 8, e2860.
Bertone, et al., "Demonstrations of Decreased Sensitivity to Complex Motion Information Not Enough to Propose an Autism-Specific Neural Etiology", Journal of Autism and Developmental Disorders, vol. 36, No. 1, Jan. 2006, Published Online: Dec. 23, 2005, pp. 55-64.
Legault, et al., 2012 (2012), "Healthy older observers cannot use biological-motion point-light information efficiently within 4 m of themselves", i-Perception 3(2) 104-111; ISSN 2041-6695, URL http://i-perception.perceptionweb.com/journal/I/volume/3/article/i0485.
Faubert, "Professional athletes have extraordinary skills for rapidly learning complex and neutral dynamic visual scenes", Scientific Reports 3, Article No. 1154, Published: Jan. 31, 2013 (Jan. 31, 2013), URL http://www.nature.com/ srep/2013/13012 9 /srepO 1154/ full/srepO 1154 .html.
Legault et al., "Perceptual-cognitive training improves biological motion perception: evidence for transferability of training in healthy aging", Neuroreport: May 30, 2012 (May 30, 2012), vol. 23, Issue 8, p. 469-473, URL http://journals.lww.com/neuroreport/Abstract/2012/05300/Perceptual_cognitive_training_improves_biological.2.aspx.
Legault et al., "Healthy Older Observers Show Equivalent Perceptual—Cognitive Training Benefits to Young Adults for Multiple Object Tracking", Front. Psychol., Jun. 2013, vol. 4, Article 323, Published Jun. 6, 2013 (Jun. 6, 2013), URL http://journal.frontiersin.org/Journal/1 O .3389/fpsyg.2013 .00323/full.

SYSTEM AND METHOD FOR DETERMINING A PERCEPTUAL-COGNITIVE SIGNATURE OF A SUBJECT

TECHNICAL FIELD

The present disclosure relates to the field of perceptual-cognitive abilities of subjects. More specifically, the present disclosure relates to a system and a method for determining a perceptual-cognitive signature of a subject.

BACKGROUND

One of the most formidable tasks for the brain of an athlete during game play is to perceive and integrate complex moving patterns while allocating attentional resources in different key areas of the dynamic scene. The athlete needs to integrate information over variable visual field areas, without attending only to a small area. Furthermore, movements of the players and the object of play, such as a ball or a hockey puck, can be extremely fast and variable. For example, the ball or the hockey puck can abruptly change speed and direction. Trajectory paths of these elements can also be quite unpredictable, with sudden changes in direction and shape, with numerous occlusions and segmentations, such as objects blocking the view of others or disappearing from view. As the level of the sport increases, the rapidity at which these mental tasks must to be performed also increases. Notwithstanding basic physiological capabilities and hard work, the combination of complexity and speed of the perceptual-cognitive processing required by athletes may potentially be one of the main determining factors as to whether athletes will graduate to and function well at superior levels.

In a different field of endeavor, elderly people or persons having suffered from trauma may have cognitive impairments that affect their perceptual-cognitive abilities. Their ability to perform everyday tasks, for example driving a car or walking in a crowd, may suffer from those cognitive impairments.

A method and a device for assessing, training and improving perceptual-cognitive abilities of subjects is described in PCT publication no WO 2010/037222 A1 to Faubert and Tinjust, published on Apr. 8, 2010 (hereinafter "Faubert'2010"), the disclosure of which is incorporated by reference herein in its entirety. The teachings of Faubert'2010 can be applied to athletes as well as to anyone suffering from cognitive impairments.

Faubert'2010 describes a variety of parameters, including a number and speed of targets moving on a display for tracking and identification by a subject under test. Of course, these parameters will vary greatly according to the particulars of the specific subject and according to the subject's rate of progress when undergoing training.

Therefore, there is a need for a system and a method for determining a perceptual-cognitive signature of a subject for optimally setting parameters according to a subject's perceptual-cognitive training needs.

SUMMARY

According to the present disclosure, there is provided a system for determining a perceptual-cognitive signature of a subject. The system comprises a display, an interface and a controller. The display shows a plurality of objects. The interface receives, from the subject, identifications of one or more target objects amongst the plurality of displayed objects. The controller specifies a number of target objects, sets a speed of the objects moving on the display for a predetermined duration in each of a series of core trials, and determines the perceptual-cognitive signature of the subject. The signature is determined according to the number of target objects, the predetermined duration of each of the series of core trials, and a correctness of the identifications, by the subject after each predetermined duration, of the target objects over the series of core trials.

According to the present disclosure, there is also provided a method for determining a perceptual-cognitive signature of a subject. A speed of a plurality of objects moving on a display for a predetermined duration is set in each of a series of core trials. A number of one or more target objects amongst the plurality of objects is specified. Identifications are received, from the subject, of the one or more target objects amongst the plurality of objects. The perceptual-cognitive signature of the subject is determined according to the number of target objects, the speed of the objects, the predetermined duration of each of the series of core trials, and a correctness of the identifications, by the subject after each predetermined duration, of the target objects over the series of core trials.

The foregoing and other features will become more apparent upon reading of the following non-restrictive description of illustrative embodiments thereof, given by way of example only with reference to the accompanying drawings. Like numerals represent like features on the various figures of the drawings.

BRIEF DESCRIPTION OF THE DRAWINGS

Embodiments of the disclosure will be described by way of example only with reference to the accompanying drawings, in which.

DETAILED DESCRIPTION

Figure 1:
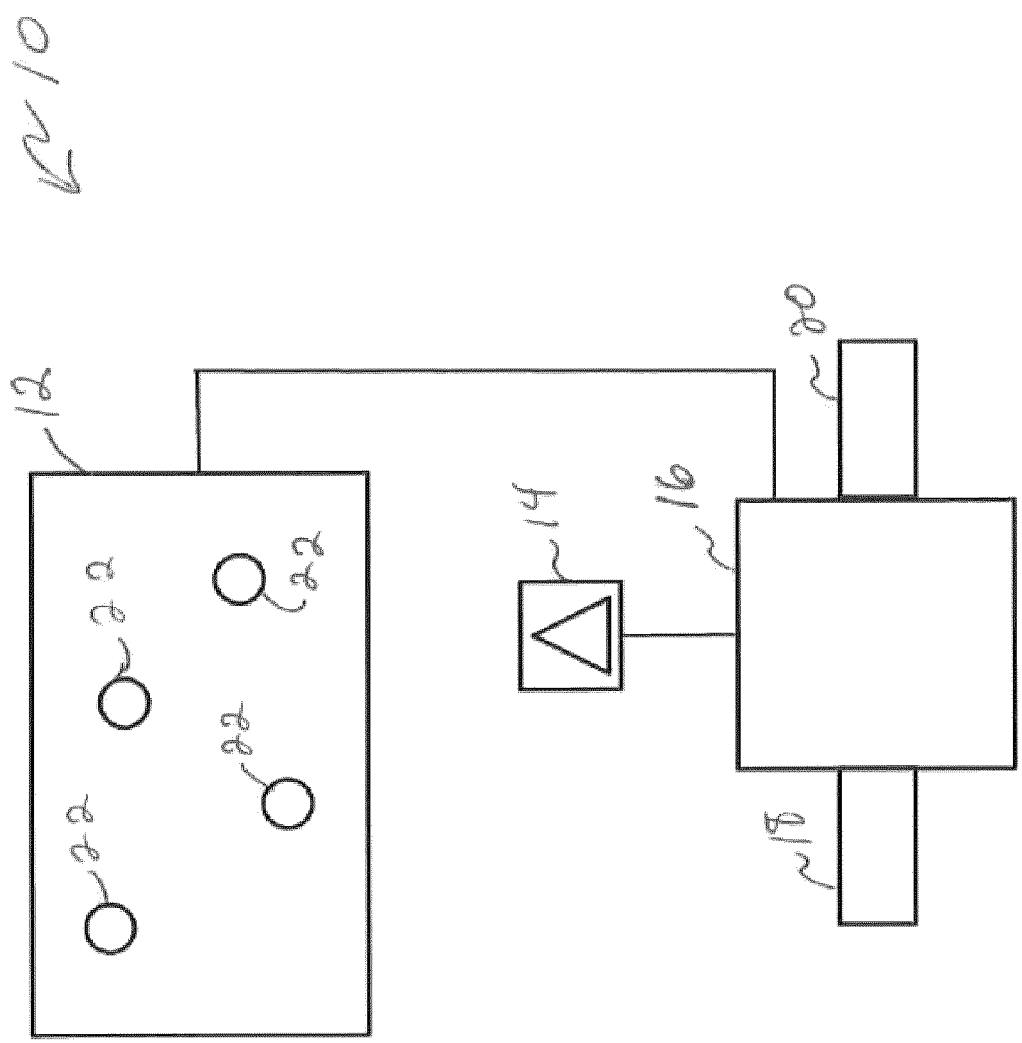
FIG. 1 is a block diagram of a system for determining a perceptual-cognitive signature of a subject.

Various aspects of the present disclosure generally address one or more of the problems of optimally setting parameters according to a subject's perceptual-cognitive training needs.

The present disclosure introduces a system for determining a perceptual-cognitive signature. Without limitation, the system can use an augmented version of the system introduced in Faubert'2010.

A perceptual-cognitive signature of a subject can be described as a characteristic pattern of performance of the subject. The signature may be determined by measuring a sensitivity of the subject to various stimuli with the aim of defining his/her level of attentional capabilities. A more detailed description of the concept of perceptual-cognitive signature is described in "Demonstrations of decreased sensitivity to complex motion information not enough to propose autism-specific neural etiology", Bertone A., Faubert J., *Journal of Autism and Developmental Disorders*, Vol. 36, No. 1, January 2006, pages 55-64, the disclosure of which is incorporated by reference herein in its entirety.

The system for determining a perceptual-cognitive signature defines a core trial that involves, for example, tracking by a subject of four (4) targets amongst four (4) distractors moving for an 8-seconds duration, 20 trials in a row. A speed threshold measurement process allows perceptual-cognitive performance of the subject to be sensitively rated on a fine grain scale. Speed thresholds according to this process are dimensionless, relative values.

As the system elicits high-level mental resources, the ability to perform the core trials varies greatly between subjects. For example, elderly people with cognitive impairments that affect attention typically obtain speed thresholds of less than 0.5 on a standardized core trial, whereas elite athletes generally score speed thresholds between 1.5 and 3.0.

Subjects on the low end of the speed threshold spectrum could receive sub-optimal conditioning if the core trial was defined with too difficult parameters for their cognitive level, creating uncertainty in the speed threshold measure. To overcome this problem, the present system for determining a perceptual-cognitive signature uses two fundamental parameters that can be altered to predictably modulate the difficulty of the core trial across the whole human performance spectrum. A first variable is a number of targets the subject needs to track. A second parameter is a duration of the core trial. Changing these two parameters allows the core trial to be matched to the training needs of a particular subject, ensuring reliable measurements.

Until now, correctly modulating the setting of core trial parameters depended on an experimental approach of guessing, testing and subjectively resetting them over multiple sessions until suitable speed thresholds were achieved.

The present system provides a solution for determining optimal parameter settings for any subject's perceptual-cognitive training. In addition, the system allows identification of specific attentional traits.

The System

Referring now to the drawings, FIG. 1 is a block diagram of a system for determining a perceptual-cognitive signature of a subject. The system 10 of FIG. 1 is simplified when compared to the system of Faubert'2010 but is nevertheless sufficient to support the determination of a perceptual-cognitive signature of a subject. The system 10 comprises a display 12, a subject interface 14, a controller 16, and may also comprise an input interface 18 and an output interface 20. The controller 16 is operatively connected to the display 12, to the subject interface 14 and, if present, to the input and output interfaces 18, 20. The display 12 may consist of a two dimensional display or of a three-dimensional (3D) display.

The controller 16, operably connected to the display 12, controls a number of objects 22 and sets a speed of this plurality of objects 22 moving on the display 12. The controller 16 also specifies a number of target objects to be tracked by the subject amongst the objects 22. The controller 16 ensures that the objects 22 move on the display 12 for a certain predetermined duration in each of a series of core trials. The subject interface 14 receives, from the subject, identifications of one or more target objects amongst the plurality of objects 22 at the end of a given core trial and provides these identifications to the controller 16. Non-limitative examples of subject interfaces 14 that can be used by the subject to identify target objects may include a real keyboard, a virtual keyboard, a mouse or like pointer device, a voice recognition system, one or more sensors mounted on the subject including motion sensors and/or positional sensors, etc. The controller 16 determines the perceptual-cognitive signature of the subject according to the number of target objects, the speed of the objects 22, the duration of each of the series of core trials, and a correctness of the identifications, by the subject after each predetermined duration, of the target objects over the series of core trials. The correctness of the identifications may be expressed as a percentage of correct identifications or as a ratio of correct identifications over a total number of possible correct identifications. The perceptual-cognitive signature of the subject defines a level of attentional capabilities of the subject.

The input interface 18, if present, is used to supply the controller 16 with parameters of the series of core trials. The output interface 20, if present, is used to output the perceptual-cognitive signature of the subject as determined by the controller 16. It is also within the scope of the present disclosure that the controller 16 supplies, through the output interface, the collected values (number of target objects, speed of the objects 22, duration of each of the series of core trials, and correctness of the identifications) to an external and/or distant computer, eventually through a communication link, for determination of the perceptual-cognitive signature of the subject and also for other possible processing of these collected values.

Figure 2:
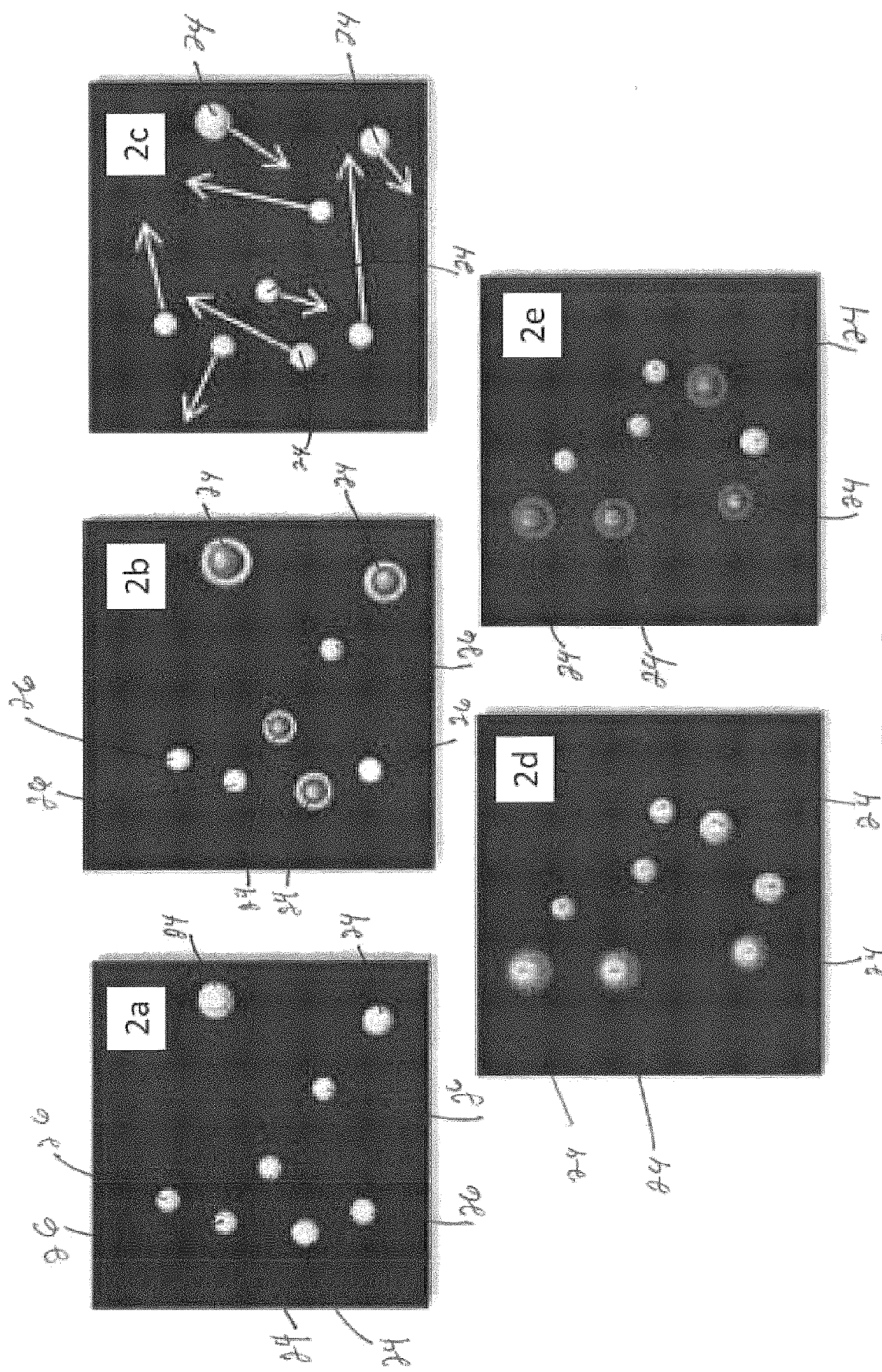
FIG. 2 is an illustration of five phases in an example of perceptual-cognitive core trial.

FIG. 2 is an illustration of five phases in an example of perceptual-cognitive core trial. The objects 22 introduced in the foregoing description of FIG. 1 are illustrated as four (4) target objects 24 (spheres) surrounded by four (4) additional spheres that need not be tracked but act as distractors 26. View 2a shows eight (8) randomly positioned objects 22 (spheres), including the target objects 24 and the distractors 26, presented on a display, for example in a virtual volumetric space if the display offers 3D capabilities. View 2b shows a visual identification of the four (4) particular target objects 24, which are the spheres to be tracked in the course of the core trial. The identification is shown for a brief period, for example one second. View 2c shows that the identification has been removed and all spheres move, for example, with dynamic interactions for a predetermined duration. During this movement, the spheres can collide and consequently suddenly change direction. Alternatively, spheres can cross over other spheres, thus temporarily occluding their view. In view 2d, the subject identifies the four (4) target objects 24 that have been tracked. Finally, in view 2e, feedback is provided to the subject by identifying the four (4) target objects 24 that needed to be tracked. The views of FIG. 2 illustrate an accurate identification by the subject. If the subject has correctly identified all four (4) spheres, the core trial may be repeated at a faster speed of movement. On the other hand, if the subject has not correctly identified all four (4) spheres, the core trial may be repeated at a slower speed of movement. Processes within the core trial can thus be repeated following a speed staircase procedure, defined hereinbelow, until a speed threshold is ultimately established.

FIG. 2 shows an example in which the number of distractors 26 is equal to the number of target objects 24. In a particular realization, the controller 16 may control the display 12 to show more or less distractors 26 and more of less target objects 24 than as illustrated on FIG. 2. Additionally, the number of distractors 26 may be larger or smaller than the number of target objects 24. FIG. 2 shows eight (8) objects 22 for illustration purposes without limiting the present disclosure.

Figure 3:
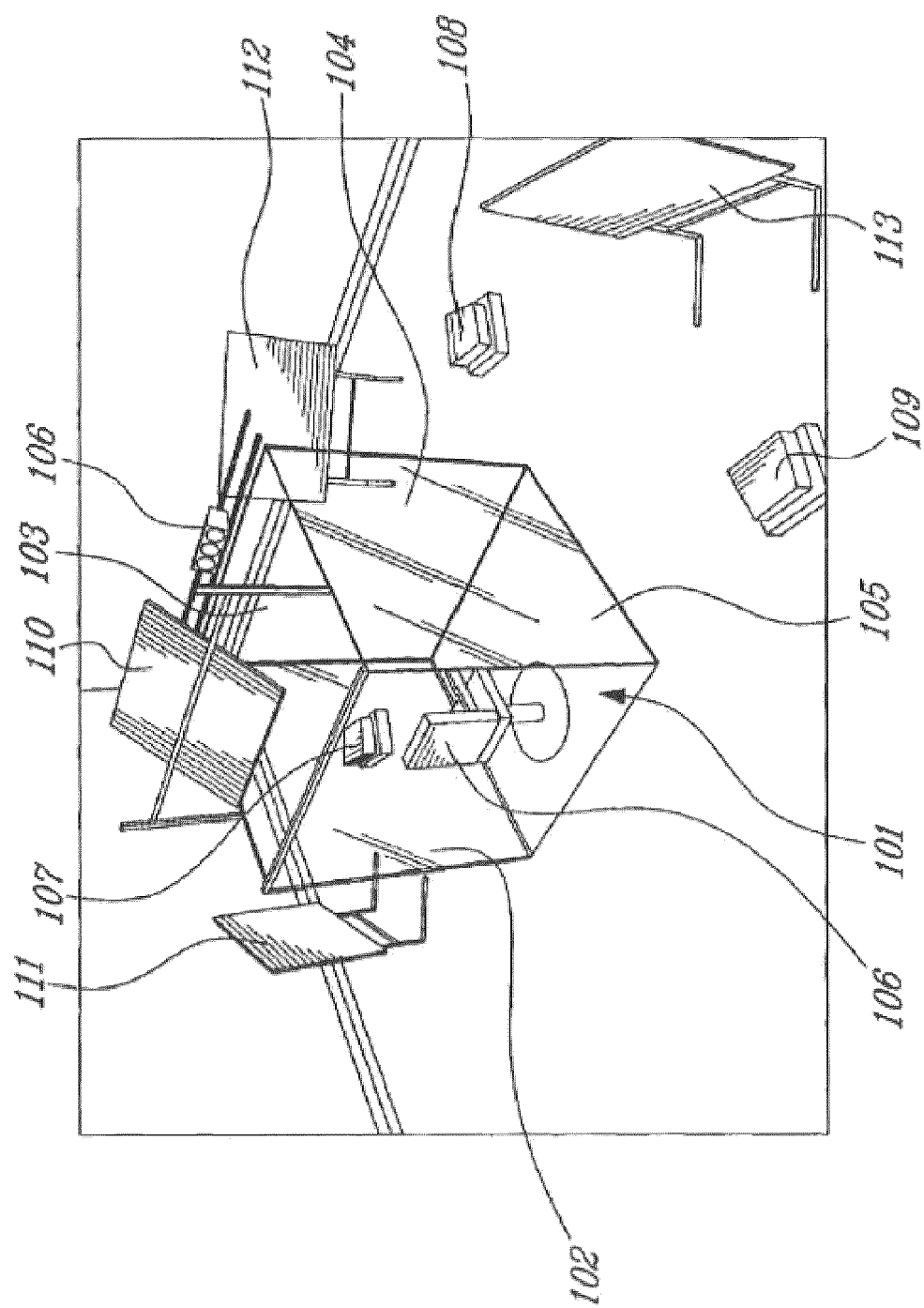
FIG. 3 is a perspective view of an example of the system of FIG. 1 comprising a full immersive virtual environment.
Figure 4:
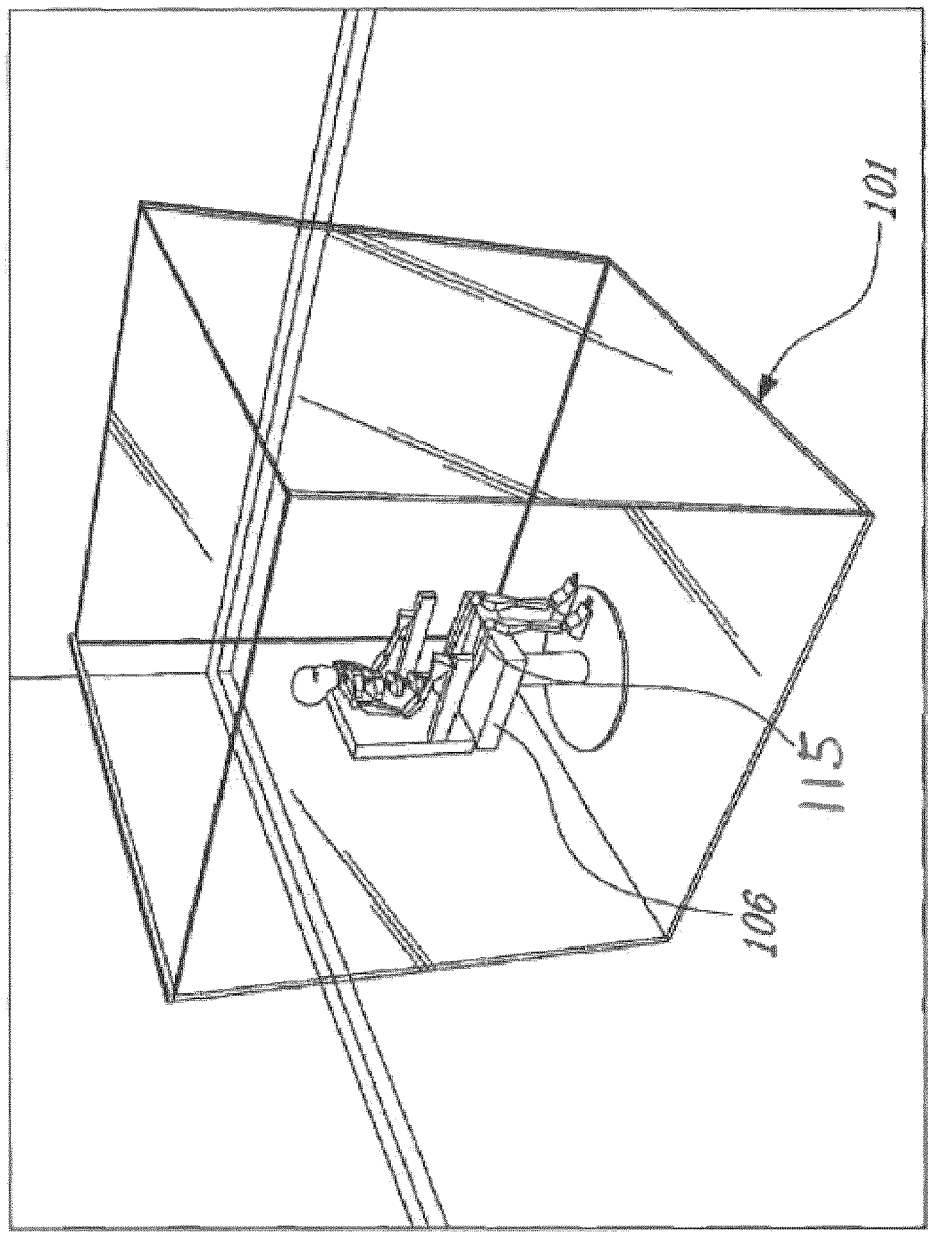
FIG. 4 is a perspective view illustrating a position of a subject in the environment of FIG. 3.

Returning to FIG. 1, the display 12 can be realized as a 3D display or as a head-mounted display (HMD). A variant of the system 10 may alternatively integrate a full immersive virtual environment. FIG. 3 is a perspective view of an example of the system of FIG. 1 comprising a full immersive virtual environment. FIG. 4 is a perspective view illustrating a position of a subject in the environment of FIG. 3. The full immersive virtual environment of FIGS. 3 and 4 was introduced in Faubert'2010 and can be integrated in the system of FIG. 1. Referring at once to FIGS. 3 and 4, the display 12 of FIG. 1 is substituted with a fully immersive virtual environment (FIVE) room 101 in which the subject is fully immersed in a given three-dimensional environment and the stimuli are presented (FIG. 3). The FIVE room 101 has a size of, for example, 8×8×8 feet and comprises four (4) projection surfaces (three walls 102, 103 and 104 and a floor 105). The display displays stereoscopic images on the four (4) projection surfaces (the three walls 102, 103 and 104 and floor 105) to form the given 3D environment in which virtual objects are presented. The display comprises, for that purpose, projectors 106, 107, 108 and 109 and associated planar reflectors 110, 111, 112 and 113, respectively to project and display the images on the four (4) projection surfaces (the three walls 102, 103 and 104 and floor 105) under the control of a display controller, for example under the form of a computer (not shown). An ophthalmologic chair 106 positioned substantially in a central position of the FIVE room 101 (FIG. 4)) is provided to sit the subject such as 115.

The Attention Test Series

The system of FIG. 1, possibly including the environment of FIGS. 3 and 4, supports a battery of three (3) types of attention test series: selective attention, sustained attention and stamina attention. These are specialized parameter variations of the core trial that vary in ways that emphasize specific perceptual-cognitive demands and that are integral to attentional performance and certain neurobiological alterations.

A full assessment of a subject takes approximately 30 minutes to complete. There are six (6) test components, including up to four (4) components for the selective attention test series, one for the sustained attention test series, and one for the stamina attention test series. Each test component provides progressive profiling, such that the result of each test component determines which test is used next or to set the test's fundamental parameters. For example, the selective attention test series determines the speed and number of targets set for the sustained attention test series.

The results of each of the three types of test series provide measurements specific to selective attention, sustained attention, and attention stamina. The variation between these scores relative to each other will provide a perceptual-cognitive signature of the distinct attentional traits of each subject. These are expected to correlate significantly to real-world cognitive abilities and neurobiological disorders. For example, a child with attention deficit hyperactivity disorder may be more likely to have low selective attention, very low sustained attention, and normal attention stamina.

Determination of the perceptual-cognitive signature of a subject is also useful in setting specialized training sessions that more strongly emphasize conditioning of the type of attention that a subject is weak in, for example adding selective attention test series sessions to more rapidly overcome a weakness in selective attention.

The assessment results can be used as a profile to determine parameters and conditions for test components within the assessment, and to optimize the setting of long term training programs by catering specifically to the attentional needs of subjects. The results can also reveal signatures of attentional capabilities that may relate directly to a range of neurobiological conditions.

Using a sequence of core trials, for example involving multiple object tracking (MOT) in 3D, and one ball tracking tests with varying parameters, three (3) types of attention will be progressively assessed through three specialized tests: 'selective attention', 'sustained attention', and 'stamina attention'. Perceptual-cognitive attributes relevant to specific attention capabilities can then be emphasized in each of the testing phases. Periodic reassessments throughout the training program can also be used to adapt to evolving training needs.

A subject's perceptual-cognitive signature and training program is revealed within a 30 minutes assessment. An approach tailored to a particular subject facilitates specific improvements in the subject's perceptual-cognitive abilities. Along with other assessments, the results may assist in determining and discovering specific attention related disorders.

Figure 5:
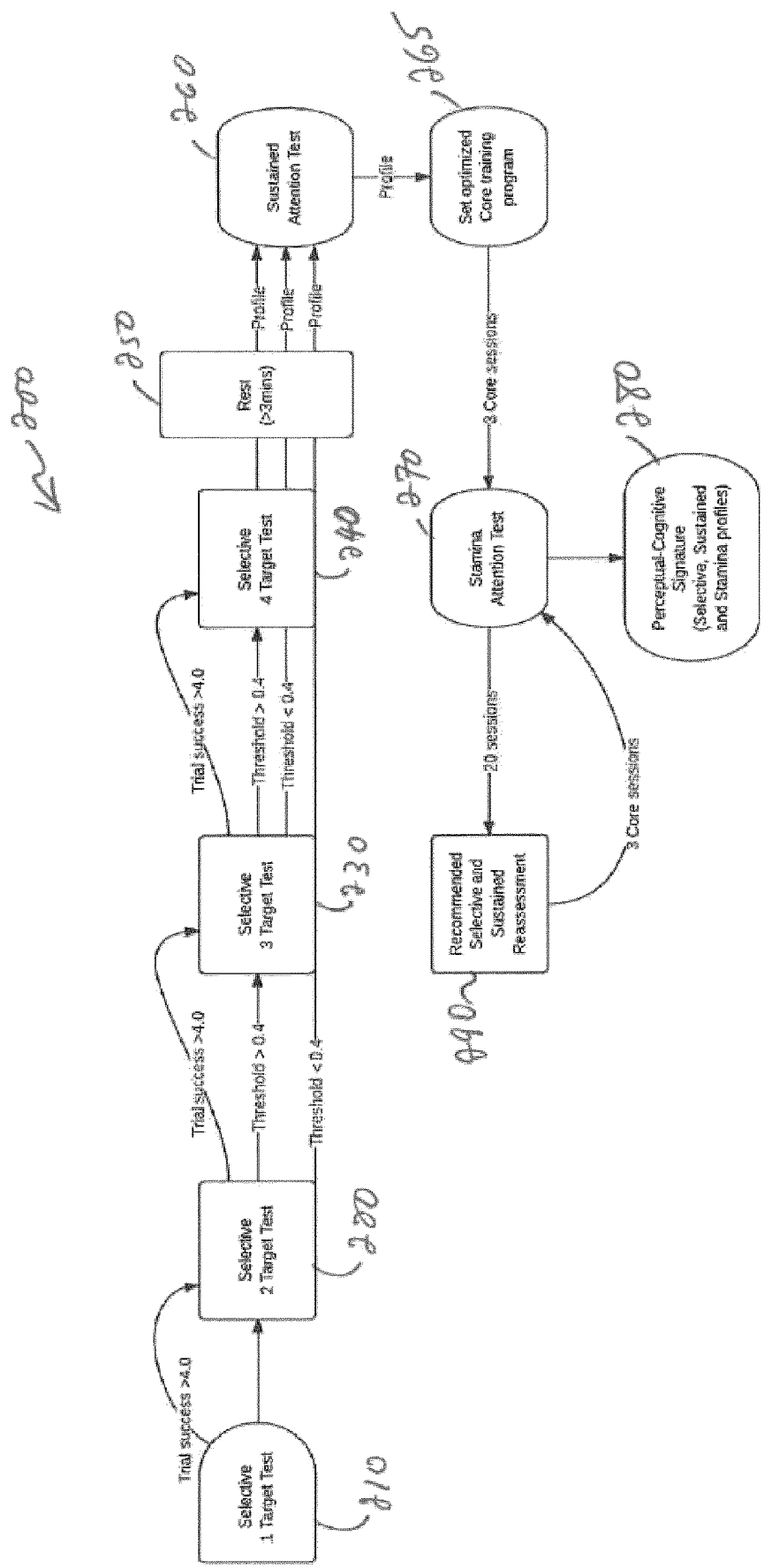
FIG. 5 is an overall view of a perceptual-cognitive assessment process.

FIG. 5 is an overall view of a perceptual-cognitive assessment process. A perceptual-cognitive assessment process 200 is performed by the system 10 under the control of the controller 16. The process 200 comprises a plurality of operations that may be executed in variable order, some of the operations possibly being executed concurrently, some of the operations being optional. The process 200 includes up to four (4) selective attention test series 210, 220, 230 and 240, a pause 250, a sustained attention test series 260, and a stamina attention test series 270. In each test series, a variable speed of objects 22 shown moving on the display 12 is adjusted by the controller 16. As mentioned hereinabove, speed values and speed threshold values are expressed in dimensionless, relative terms. Later Figures will provide details of the operation of each type of attention test series.

The selective attention test series 210 involves one (1) single target object to be tracked, shown to the subject on the display 12. If the subject has very high capabilities and provides accurate identification of the target object at a speed greater than 4, the selective attention test series 210 is immediately stopped and the process moves to the selective attention test series 220. Otherwise all core trials of the selective attention test series 210 are executed and the process moves to the selective attention test series 220. The selective attention test series 220, 230 and 240 respectively use two (2), three (3) and four (4) target objects shown to the subject on the display 12. If the subject provides accurate identification of the target objects at a speed greater than 4 in any of the selective attention test series 220 or 230, execution of that test series is stopped and the process moves to the next test series. If the subject fails to meet a pass speed threshold of 0.4, the process immediately moves to the pause 250. Otherwise, the process moves from one test series to the next when the subject achieves a consistent speed that exceeds the pass speed threshold of 0.4. The pause 250, lasting at least three (3) minutes, follows a last successful test series, after which parameters comprising a speed value obtained by the subject for a given number of target objects (between 1 and 4 target objects) are used to determine a profile for the sustained attention test series 260.

Results of the selective and sustained attention test series are used in operation 265 to determine a profile for setting a personal core training program. A core baseline, based on three (3) core sessions in which the identifications of the one or more target objects are correct, is used to determine a profile for setting parameters for the stamina attention test series 270. A perceptual-cognitive signature 280, including a selective profile, a sustained profile and a stamina profile, is obtained from results from the selective, sustained and stamina attention test series. Reassessments 290 can be used to adapt the training program of the subject according to his perceptual-cognitive improvements and to obtain new signatures over time.

The Selective Attention Test Procedure

The purpose of the selective attention test procedure is to measure selective attention abilities in a focused way by progressing from very low level tracking with few dynamic or distributed attention demands, upwards to more target objects, increasing selective attention difficulty. The procedure uses short predetermined durations of object movements, for example six (6) seconds, in order to minimize sustained attention demands. Testing across different numbers of target objects allows selective attention to be measured comparatively at various levels relative to the subject's performance.

The progressive gradation in the number of target objects is directly relevant to determining the number of target objects suitable for a subject's core training program.

If a subject's speed threshold result for the selective attention test series 220 or 230 is lower than the pass speed threshold of 0.4, proceeding to the next selective attention test series 230 or 240 is not attempted since the subject has already reached his maximum capability in terms of number of tracked target objects. If a trial speed greater than 4 is attained for any one of the selective attention test series 210, 220 or 230, the current test series ceases and the process moves to the next selective attention test series with one additional target object. If however the subject then scores less than the pass speed threshold in the next selective attention test series, the process returns to the previous test series, regardless of the fact that the previous result exceeded the speed of 4.

There is no minimum speed threshold required for progressing from the selective attention test series 210 to the selective attention test series 220. This is because single object tracking elicits significantly different mental resources than multiple object tracking. In effect, a result obtained in the selective attention test series 210 may not be a stable indicator of multiple object tracking performance (unlike comparisons of performance obtained between 2, 3, and 4 target objects). Accordingly, results of the selective attention test series 210 may contribute special information towards the perceptual-cognitive signature, for example by isolating issues related to foveal tracking or by confirming that certain motion tracking deficiencies are not specific to multiple object tracking.

Figure 6:
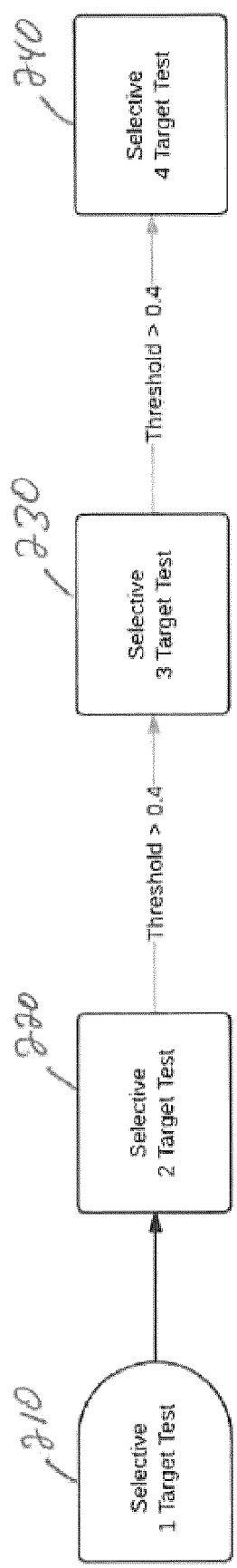
FIG. 6 is a sequence diagram of a selective attention test procedure.
Figure 7:
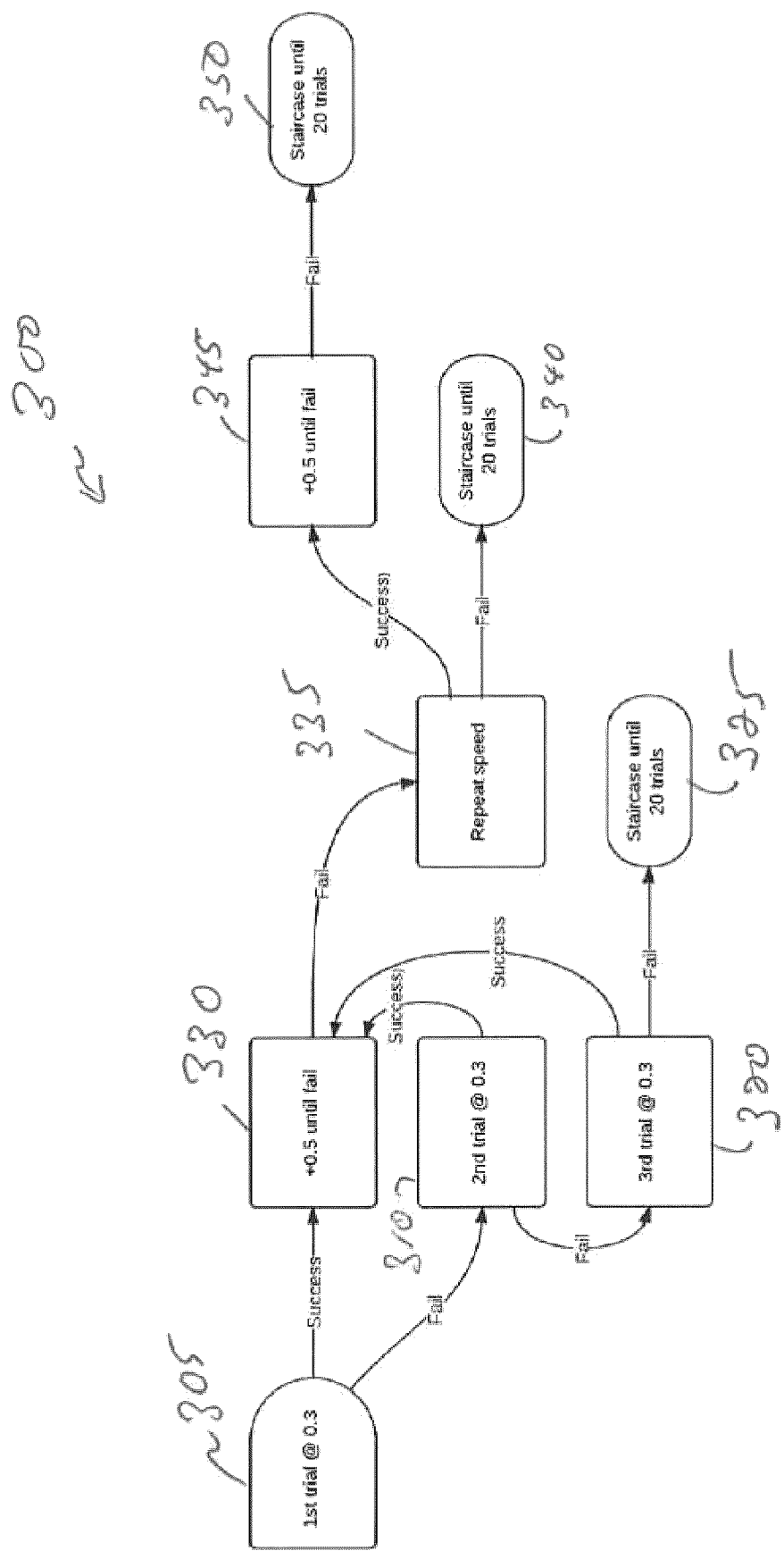
FIG. 7 is a sequence diagram detailing a core trial of the selective attention test procedure of FIG. 6.

FIG. 6 is a sequence diagram of a selective attention test procedure. FIG. 7 is a sequence diagram detailing a core trial of the selective attention test procedure of FIG. 6. FIG. 6 shows a typical sequence in which a subject having good, but not exceptional perceptual-cognitive capabilities moves from one test series to the next within the selective attention test series 210, 220, 230 and 240, at least meeting the pass speed threshold in each test series. A core trial 300 of FIG. 7 shows detailed operations applicable to any of the selective attention test series 210, 220, 230 and 240. The core trial 300 comprises a plurality of operations that may be executed in variable order, some of the operations possibly being executed concurrently, some of the operations being optional.

The core trial 300 is initiated by defining a first trial 305 with a speed set at 0.3, this speed being defined to accommodate a subject having very low perceptual-cognitive abilities. A good answer requires correct identification of all target objects. All other responses are considered as wrong. If the subject fails to correctly identify the one or more target objects in the core trial 300 (i.e. between 1 and 4 target objects, depending whether the present core trial 300 is part of the selective attention test series 210, 220, 230 or 240), a second trial 310 at the same speed is attempted. If the second trial 310 fails, a third trial 320 at the same speed is attempted. If the third trial fails, the core trial 300 ends with a staircase procedure 325, which is described hereinbelow. If any of the first, second or third trial 305, 310 or 320 succeeds, the core trial 300 continues with operation 330 in which the speed is stepped by adding 0.5 to the current speed in each of consecutive trials until a trial fails at a last speed level; this fairly large (0.5) speed step is selected to allow subjects having superior capabilities to rapidly reach their actual speed thresholds. Following a failed trial in operation 330, a retrial 335 at that last speed level is attempted. If the subject fails the retrial 335, the core trial 300 ends with a staircase procedure 340. If the subject successfully passes the retrial 335, the core trial 300 continues with operation 345 in which the speed is stepped again by adding 0.5 in each consecutive trial until a trial fails at a last speed level. The core trial 300 then ends with a staircase procedure 350.

To execute the staircase procedures 325, 340 and 350, the controller 16 uses an adaptive protocol to vary (up or down) the speed of the objects 22 moving on the display 12. The controller 16 adjusts the speed of the objects 22 from one trial to the other in relation to the accuracy of responses of the subject to successive trials. A staircase speed variation can be set with four (4) inversions (an inversion being defined as changing from an up variation to a down variation or changing from a down variation to an up variation), or three (3) inversions in the event of a first fail at a speed of 0.5. For example, before a second inversion, the speed of the objects 22 is increased (good answer) or decreased (wrong answer) by a factor of +0.5 at each trial. From a second inversion to a fourth inversion, the speed of the objects 22 is increased (good answer) or decreased (wrong answer) by a factor of 26% at each trial. The staircase procedure ends after 20 trials, following which a final speed threshold for the subject is determined, for the particular core trial 300. The staircase procedures 325, 340 and 350 differ from one another mainly in terms of initial speed thresholds reached by the subject.

The Sustained Attention Test Procedure

The purpose of the sustained attention test procedure is to set an appropriately challenging level of tracking for the subject and then find a duration that matches a subject's sustained tracking speed threshold. In addition, performance of the subject is measured in terms of the total numbers of target objects successfully identified throughout the sustained attention test relative to a fixed speed. Using an overload formula, described hereinbelow, this measure is converted to an approximate core speed threshold. This allows a basic performance comparison between selective attention test series versus sustained attention test series.

The sustained attention test series may use, for example, the following parameters:
- 20 trials at predetermined speed that is fixed for all trials;
- a predetermined number of target objects; and
- a varying length of trial time dependent upon trial successes or failures.

The number of target objects is determined from the selective attention test series that the subject progressed to and achieved a success speed threshold. The success speed threshold is greater than the pass speed threshold, being set for example at 0.7. If the subject progressed in terms of number of target objects, but failed achieved the success speed threshold, then the number of target objects of the previous selective attention test series is used. Otherwise stated, meeting the pass speed threshold (e.g. reaching a speed of 0.5, thus exceeding the pass speed threshold of 0.4) is required for progressing to the next selective attention test series while meeting the success speed threshold (e.g. 0.7) is required for setting the sustained attention test series parameters. The speed is set based on the speed threshold value achieved for the same selective attention test series that the number of target objects is derived from, which may be modified by an increase of up to 10% to accommodate for improvements between tests.

Figure 8:
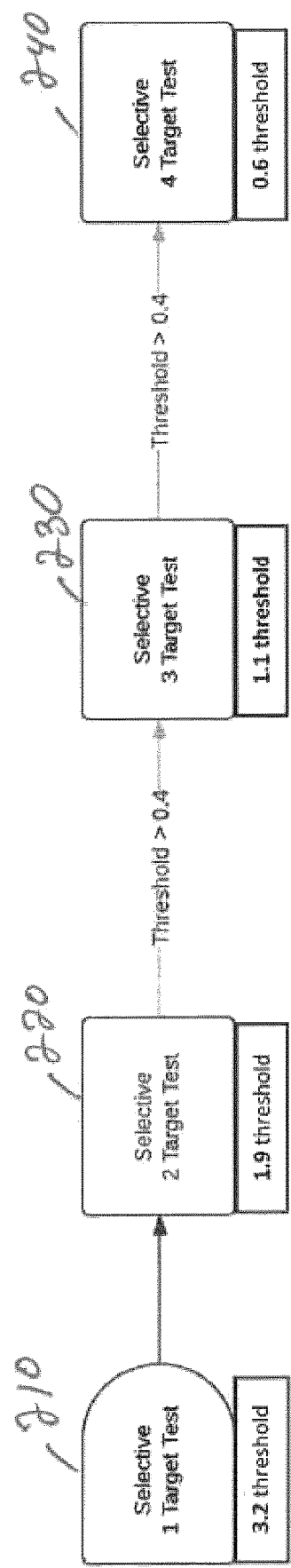
FIG. 8 is a sequence of example speed thresholds obtained when executing the selective attention test procedure of FIG. 6.

FIG. 8 is a sequence of example speed thresholds obtained when executing the selective attention test procedure of FIG. 6. In this example, the subject progressed to four (4) target objects, exceeding the pass speed threshold of 0.4 in all selective attention test series 210, 220, 230 and 240. However, the subject failed to meet the success speed threshold of 0.7 in the last selective attention test series 240. Consequently, the sustained attention test series 260 will use as parameters three (3) target objects and a fixed speed set at 1.1, which is the speed threshold reached by the subject in the selective attention test series 230.

Results obtained in the sustained attention test procedure allow differentiating levels of sustained attention between subjects, for identifying perceptual-cognitive signature characteristics and for profiling purposes. The results can also be used to determine an optimal trial time duration to be used for a core training program.

Figure 9:
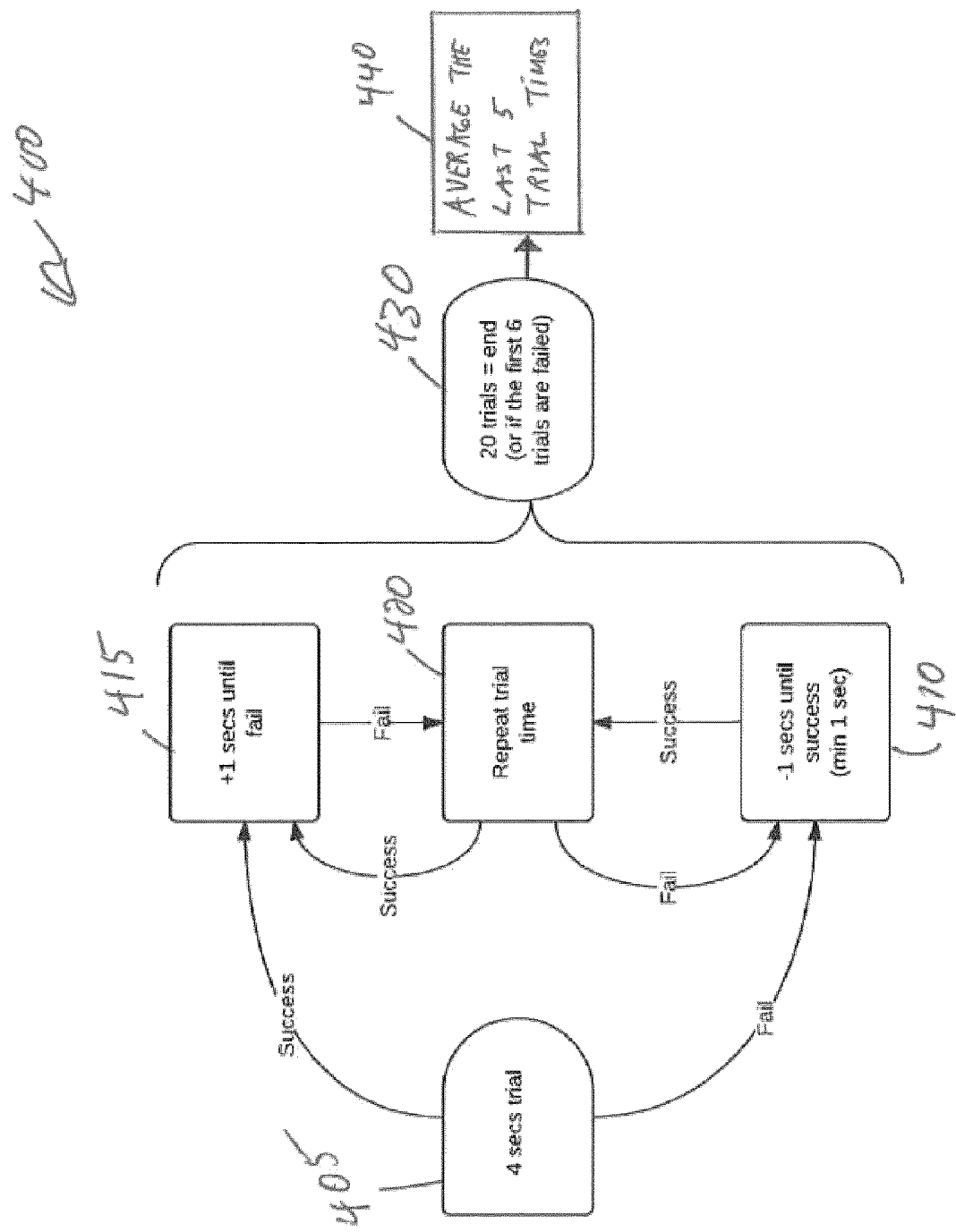
FIG. 9 is a sequence diagram detailing a trial of a sustained attention test procedure.

FIG. 9 is a sequence diagram detailing a trial of a sustained attention test procedure. A trial 400 of FIG. 9 shows detailed operations applicable to the sustained attention test series 260. The trial 400 comprises a plurality of operations that may be executed in variable order, some of the operations possibly being executed concurrently, some of the operations being optional. The trial 400 begins with a first trial 405 having a 4-seconds duration.

If the subject fails the first trial 405, a next trial 410 takes place, reducing the duration by one second in each of successive trials until the subject correctly identifies the one or more target objects defined in the sustained attention test procedure, without reducing the trial duration to less than one second. If the subject succeeds in the first trial 405, a next trial 415 takes place, increasing the duration by one second in each of successive trials until the subject fails. Following a success of the trial 410 or following a failure of the trial 415, operation 420 repeats that last trial with a same speed. Depending on the success or failure of the trial of operation 420, the trial 400 continues with operation 415 or 410, increasing or decreasing the duration of the next trial by one second. Operation 430 terminates the trial 400 when 20 trials have been attempted. At that time, the subject will have zoned into a trial duration near his sustained attention threshold, i.e. a trial duration threshold when tracking at an optimized number of targets and speed. Operation 440 determines a sustained attention tests result by averaging a duration of the last few trials, for example averaging durations of the last five (5) trials. Operation 440 may optionally round down this average duration to the nearest second.

Optionally, operation 430 can terminate the trial 400 when six (6) consecutive trials have failed. In this case, the selective attention test procedure may be executed again in order to determine more suitable parameter settings for the sustained attention test procedure for the subject.

The Stamina Attention Test Procedure

The stamina attention test procedure allows the identification of a quantity of trials that a subject can manage while maintaining a given speed threshold level, directly after completing a core session. This quantity is determined by an attention breakdown, whereby a critical cluster of trial failures ends the test. A result of the stamina attention test procedure is the total number of trials achieved relative to a personalized fixed speed of tracking and number of target objects.

To ensure that the stamina attention test procedure reliably measures attention stamina of the subject, the procedure uses a fixed speed value based on the core baseline. This is achieved by first using the selective and sustained attention test procedures to set the subject at optimal core parameters for number of target objects and duration of trials. Then completion of a minimum of three (3) core training sessions allows determination of a solid baseline measure.

To standardize the ratio of tracking time to non-tracking time during the stamina attention test procedure, the subject is asked to try and select his responses to each trial within 10 seconds, optionally being guided by a subtle timing bar presented on the display 12. Trials where answering time is exceeded by 10 seconds are recorded, along with the total answering time of the test. Answer time data may also be used to analyze attention stamina.

The subject follows the stamina attention test procedure after completing the selective attention test series 210, 220, 230 and 240 (or at least some of these series), the sustained attention test series 250, and a training program comprising a minimum of three (3) core sessions, in which the number of target objects and the trial duration are determined at operation 265 (FIG. 5) by results of the selective and sustained attention test procedures.

Figure 10:
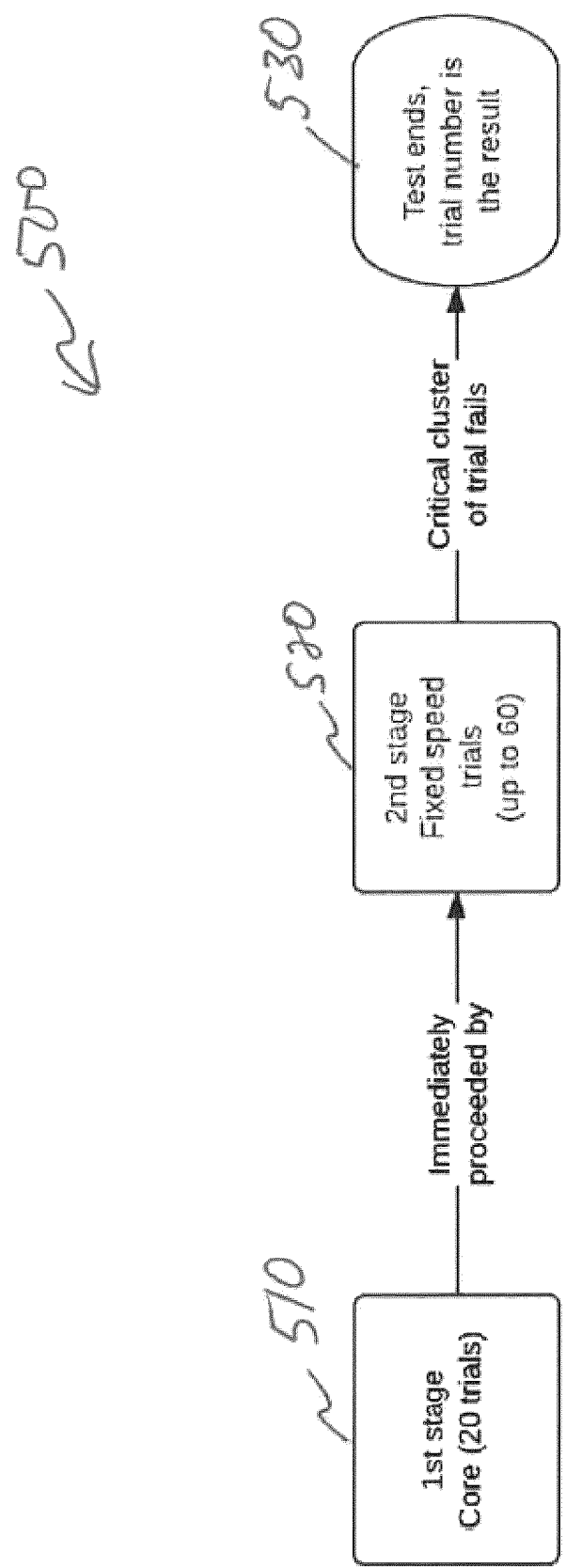
FIG. 10 is a sequence diagram of a stamina attention test procedure.

FIG. 10 is a sequence diagram of a stamina attention test procedure. The sequence 500 of FIG. 10 shows detailed operations applicable to the stamina attention test series 270. In sequence 500, the number of target objects set is the same as provided by the selective attention test result. A first stage 510 of the stamina attention test series uses parameters determined in operation 265 for a standard core session, including 20 trials with a trial duration set at 8 seconds. A second stage 520 follows, using fixed speed trials set at the average between the subject's core baseline, defined as an average of last three (3) core speed thresholds, and the core speed threshold obtained in the first stage 510 of the stamina attention test series. If however the core speed threshold falls below 30% of the value of the core baseline, the subject takes a rest for at least 3 minutes and then completes another first core session. In this case, after the subject has undergone a second core session, the average of these two (2) core sessions is then used as the fixed speed for the second stage 520 of the stamina attention test series.

The second stage 520 includes a maximum number of 60 trials. After this total of up to 60 trials within the stamina attention test series, further results would be deemed unreliable. The sequence 500 ends at operation 530 when a critical cluster of trials has failed. The critical cluster is met when an end criterion is met. The end criterion may be met when the subject has failed a number of trials within a number of last successive trials. For example, the end criterion may be met when the subject has failed a number of trials in succession, for example 3 out of 3, 4 out of 4, or 5 out of 5 trials in succession, or when the subject has failed most of a series of recent trials, for example 5 out of 6, 5 out of 7, or 7 trials in any of the last 8 trials (as a minimum measure of failure). These examples of how the end criterion can be determined at non-limiting and other criteria can be contemplated.

When the end criterion is met, for example when 3/3, 4/4, 5/5, 5/7, 6/7 or 7/8 trials are failed, the test ends at operation 530 and the total number of attempted trials of the second stage 520 provides the final result, the minimum score being 5. The fixed object speed and number of target objects used in the stamina attention test procedure may be referenced to further qualify the final result. However the number of trials alone is a relevant measure as it is achieved at the subject's own attentional speed threshold. Indeed, the general concept of stamina performance is deemed relevant when assessed in relation to the subject's own speed thresholds.

It may be observed that the stamina attention test procedure is not suitable for subjects set at a single target object tracking. Principally this is because the stamina attention test procedure is designed to measure cognitive stamina, and the foveal tracking demands with single target object tracking may be inadvertently influenced by eye muscle fatigue.

Overload Formula

An overload session trains subjects just above their core baseline speed threshold, at a fixed speed continuously for a number of trials, for example 20 or 50, or more trials. Unlike the core session, the overload session is not dependent upon trial failures. Instead, a total number of target objects correctly identified in the course of the overload session provides a basic overload result, expressed for example as 45 correct target objects identified out a possible 60 target objects, at a fixed speed set to 2.

The overload formula calculates a score for the overload session that should be an approximate equivalent of a core speed threshold, if that speed threshold is correctly determined for the subject. The overload formula adapts to both the fixed speed and the number of target objects of the overload session. For example, an overload session with two (2) target objects produces a score equivalent to a core session with two (2) target objects, even if the fixed speed is set at 1.0, 1.5, or 2.0.

The overload formula is obtained as follows:

$$T = N \times 20 \quad (1)$$

$$RT = T - TG \quad (2)$$

$$TS = TI - TG \quad (3)$$

$$TR = TS/RT \quad (4)$$

$$\text{Overload result} = TR \times S + S/OF \quad (5)$$

wherein:

T: total number of target objects in an overload session, i.e. number N of target objects defined in the overload session times 20 trials per overload session;

TG: average number of correctly identified target objects obtained from pure guessing based on statistical distribution (an empirical value for a given value of N);

RT: remaining targets;

TI: number of identified target objects;

TS: success, defined as a number of target objects correctly identified and not guessed;

TR: ratio of success; and

S: speed of the objects during the overload session:

OF: overload factor for tailoring the overload formula, OF being set empirically, having for example a value of 2 (dimensionless).

Table 1 summarizes values of T and TG for several values of N:

TABLE 1

| Number of target objects defined in an overload session (N) | Total number of target objects over 20 trials (T) | Average number of correctly guessed target objects in an overload session (TG) |
|---|---|---|
| 2 | 40 | 10 |
| 3 | 60 | 22.5 |
| 4 | 80 | 40 |
| 5 | 100 | 61 |

As an example, a subject has correctly identified 40 target objects (TI) in the course of an overload session in which the number N of target objects was 3 and the speed S of the objects was set to 2. Applying equations (1) to (5) and Table 1 yields:

$$T = N \times 20 = 3 \times 20 = 60 \quad (1')$$

$$RT = T - TG = 60 - 22.5 = 37.5 \quad (2')$$

$$TS = TI - TG = 40 - 22.5 = 17.5 \quad (3')$$

$$TR = TS/RT = 17.5/37.5 = 0.47 \quad (4')$$

$$\text{Overload result} = TR \times S + S/2 = 0.47 \times 2 + 2/2 = 1.9 \quad (5')$$

In the above, the overload factor (OL) is set to 2. The result of the overload session for the subject is therefore a dimensionless value of 1.9. This value confirms that the core speed threshold of 2 is correctly determined for the subject.

Though equation (5) is defined as an 'overload result' and has been described hereinabove as applied in the overload session, the same can also be applied to the stamina attention test series.

Staircase Performance Criteria

Criteria useful for detecting changes in performance during a staircase trial, for example due to fatigue or learning are established. Statistics have been estimated over a range of trials for four candidate criteria: (1) correlation of speed thresholds, (2) average number of target objects correctly identified, (3) average number of trials passed, and (4) change in speed threshold. Due to the mechanics of staircases, it is found that criteria #1 and #4 produce abnormal distributions that make statistical analyses difficult. However, both criteria #2 and #3 produce distributions that are well-fit by binomial distributions. Using criterion #3, it is found that a cutoff of 6/6 or 8/9 consecutive correct (or incorrect) trials can be used to detect a statistically significant increases (or decreases) in performance using a two-tailed test. Using a one-tailed test, a criterion of 5/5 or 7/8 is sufficient.

To detect changes in the speed threshold, whether due to learning or fatigue, one needs to first establish a reliable measure with a known distribution. Here, four measures are evaluated: (1) correlation, (2) average number of target objects correctly identified, (3) percent correct, and (4) change in speed. Optimally, a change in performance should be detected over fewer trials as this would provide a way to rapidly detect a change in performance. Thus the performance of these four measures is compared over a range of number of trials.

Figure 11:
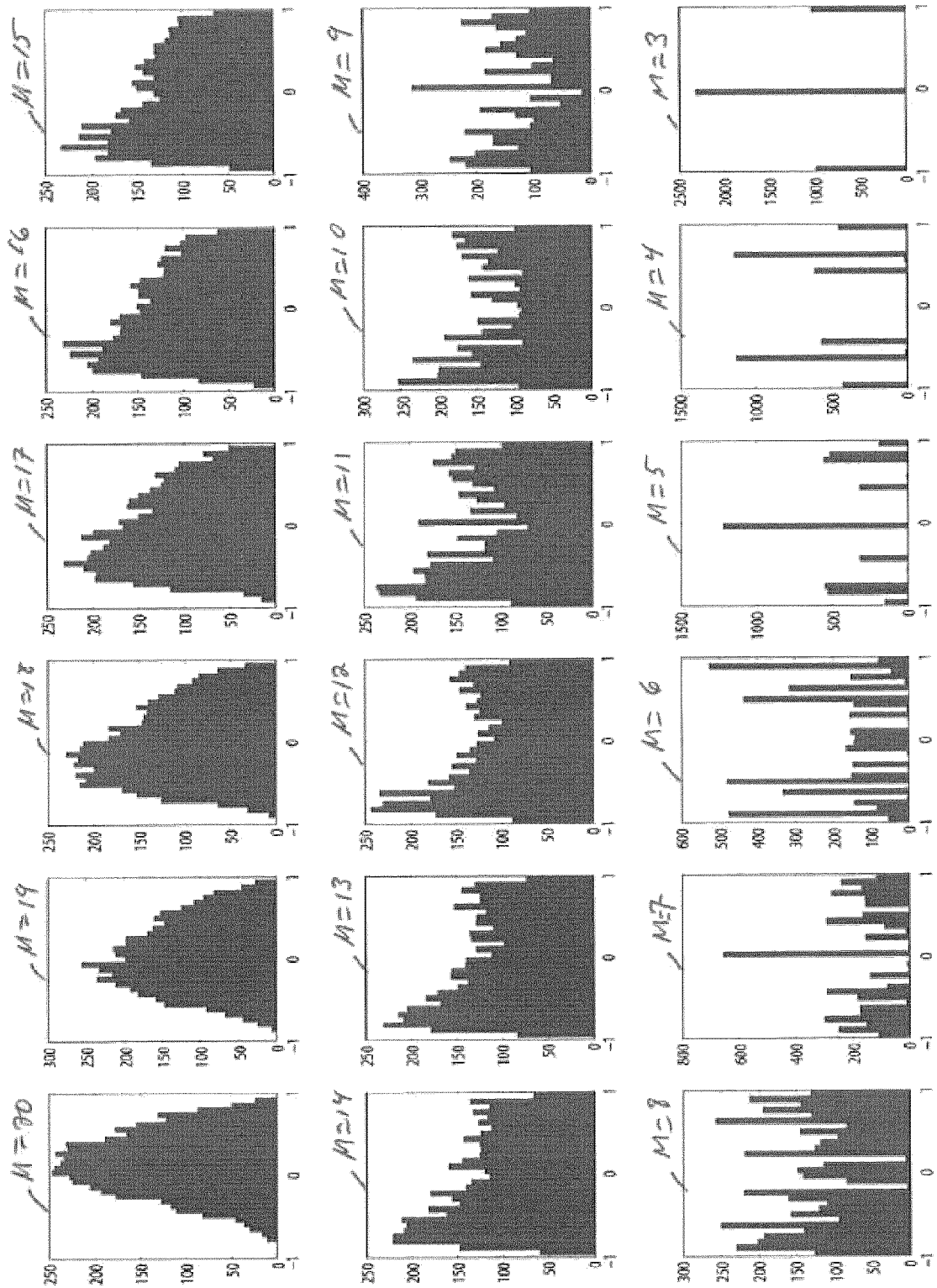
FIG. 11 is a series of graphs showing correlations between tested speed values over a plurality of trials.

A correlation of speed across trials is established. A positive (or negative) correlation would indicate that speed increases (or decreases) across trials. FIG. 11 is a series of graphs showing correlations between tested speed values over a plurality of trials. In FIG. 11, correlations are shown between tested speed values over 18 of last 20 trials, the last two (2) trials being omitted. The graphs are identified with indicia M ranging in descending number from M=20 to 3. From the trials identified as M=19 to 10, the negative bias in the distribution shows that speed thresholds tends to decrease over trials, indicating a general performance improvement. From the trials identified as M=9 to 3 trials, this performance improvement disappears, but the possible correlation values become dependent on how many trials are included, producing abnormal distributions.

FIG. 11 shows that using the correlation as a measure is not optimal because the data violates the normality assumption. Namely, the staircase used dictates that each successive trial is tested at a value one step either higher or lower than the current value. This violation of normality creates abnormal correlation distributions at low sample sizes. Even at moderate sample sizes, the distributions contain clear deviations from normality. Thus, the correlation (and slope) measure is discarded for this purpose.

Performance should remain constant as long as sampling occurs near the real speed threshold. A sudden change in performance can be used to indicate that the speed threshold has changed. Performance in this context can be measured as either (1) the average number of target objects correctly identified or the percent correct trials.

Figure 12:
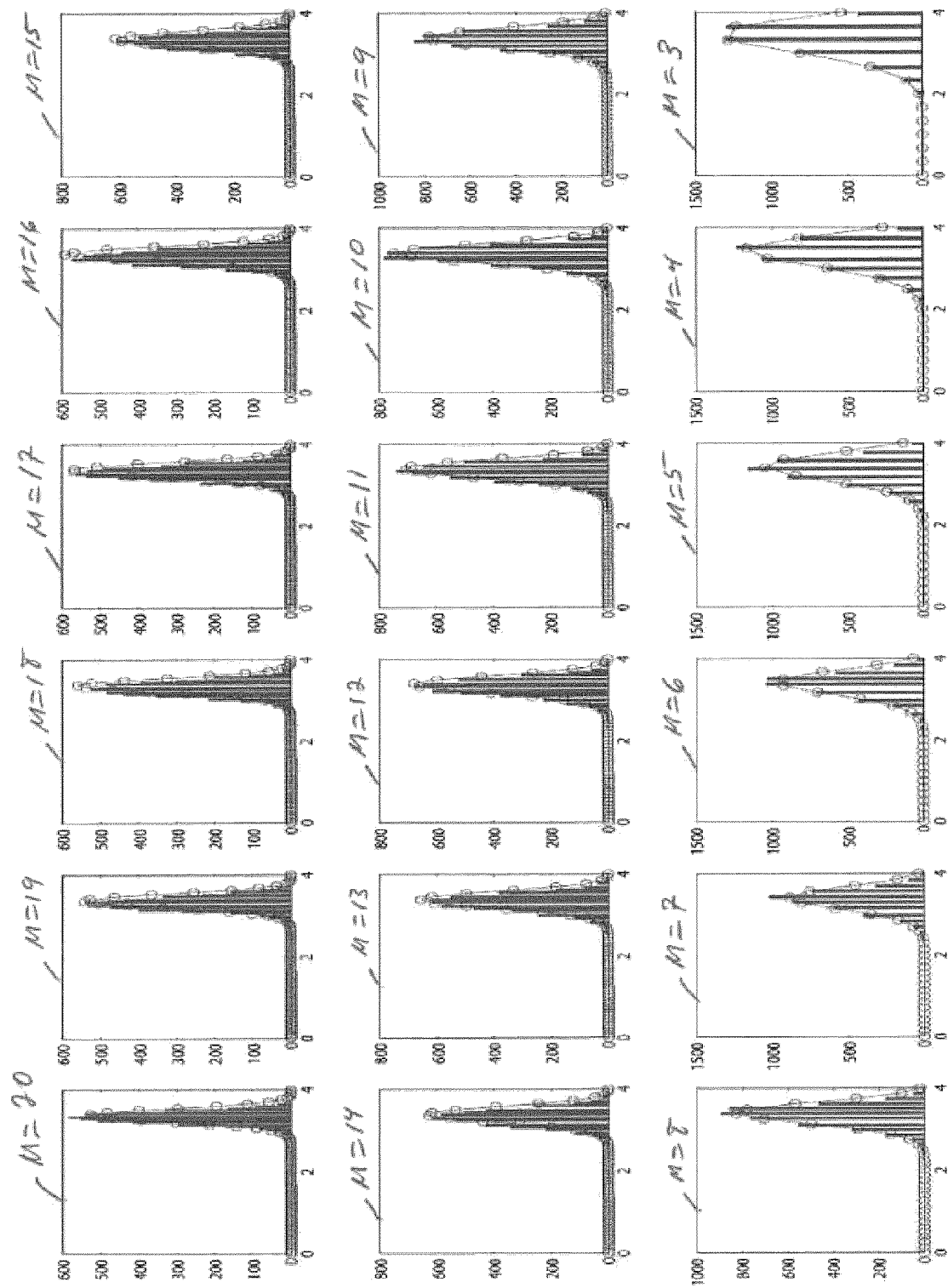
FIG. 12 is a series of graphs showing average numbers of target objects correctly identified over a plurality of trials.
Figure 13:
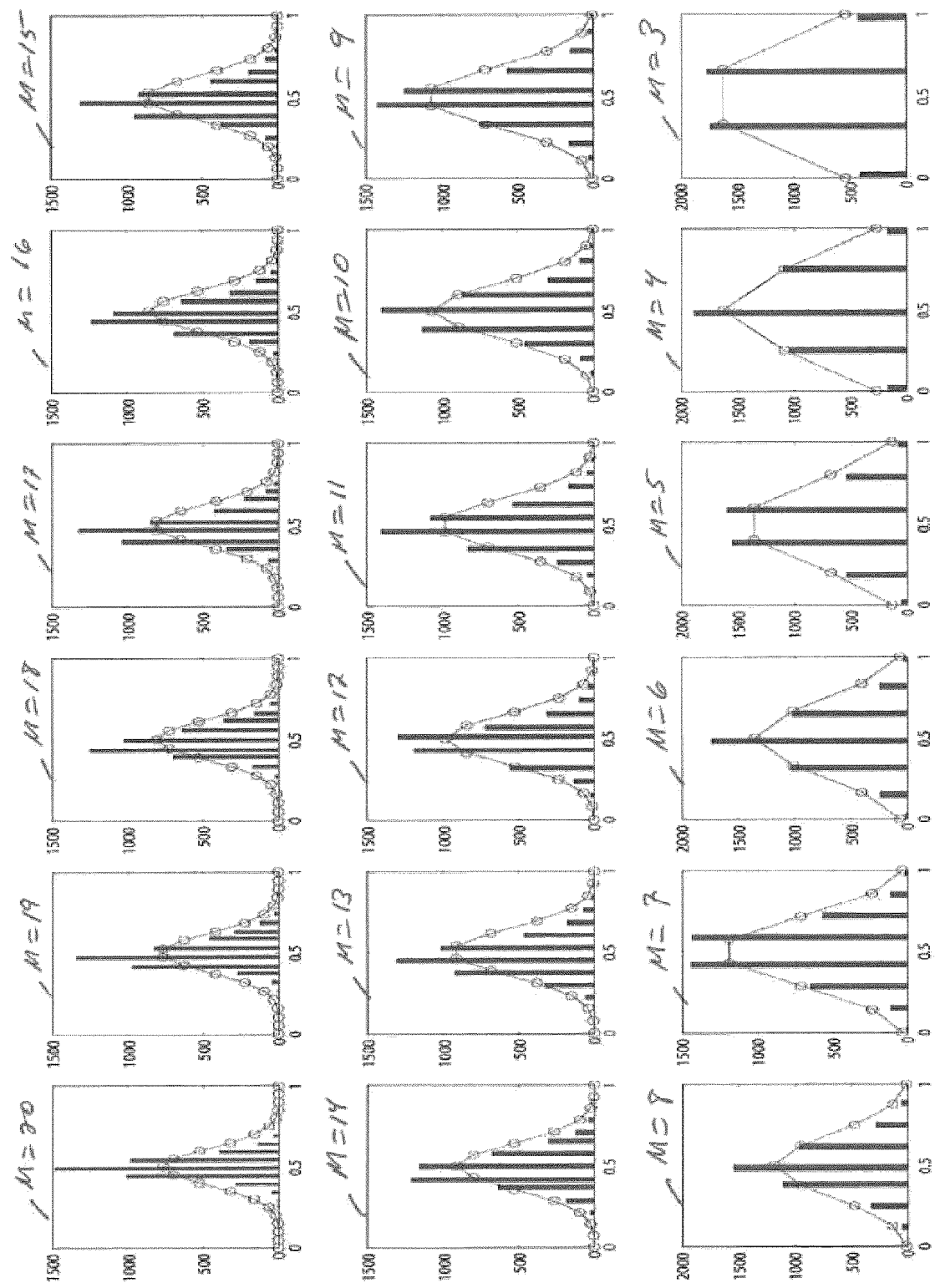
FIG. 13 is a series of graphs showing percentage of correct trials over a plurality of trials.

FIG. 12 is a series of graphs showing average numbers of target objects correctly identified over a plurality of trials. FIG. 12 shows the average number of target objects correctly identified over 18 of the last 20 trials (bars) introduced in the foregoing description of FIG. 11, and predictions using a binomial distribution (circles), shown for values of M from 20 to 3. A small central tendency bias (leptokurtic) occurs because the staircase method samples closer to the speed threshold value than assumed by the binomial distribution. FIG. 13 is a series of graphs showing percentage of correct trials over a plurality of trials. FIG. 13 shows percentages of correct trials (i.e. all target objects correctly identified) over 18 of the last 20 trials (bars), and predictions using a binomial distribution (circles), shown for values of M from 20 to 3. A small central tendency bias (leptokurtic) occurs because the staircase method samples closer to the speed threshold value than assumed by the binomial distribution.

Considering both FIGS. 12 and 13, using the average performance as a measure is feasible for two reasons: (1) the distributions are very well approximated by binomial distributions, making the detection of outliers simple using binomial distribution criteria, and (2) although the distributions do show some systematic bias (e.g. they are leptokurtic (higher peak, shallower tails) compared to the binomial distribution), the resulting error would only make our performance change criteria more conservative. The "percent correct trials" measure is preferred over the "average number of target objects correctly identified" measure because (1) the latter required the values of the binomial to be approximated, whereas the former has set values defined by the staircase, (2) the former is more closely tied to how speed threshold changed as a function of the trial, and (3) the former is symmetric over the last trials making detection of changes in performance symmetric as well.

Table 2 shows the probability of a string of hits (or misses). The column titled "2p" should be compared to the desired alpha level for a two-tailed test. The column titled "p" can be used for one-tailed tests. These values are not corrected for family-wise error (i.e. the accumulated error of testing every set of K consecutive trials). Given that these estimates are conservative due to the leptokurtic bias discussed above, it is suggested that these uncorrected criteria are acceptable unless testing sessions become very long. For one-tailed tests (e.g. due to a drop in focus), criteria of 5/5 or 7/8 are acceptable (e.g. 5 consecutive trials are incorrect, or at least 8/9 consecutive trials are incorrect). For two-tailed tests, criteria of 6/6 or 8/9 consecutive trials are acceptable.

TABLE 2

| K | p | 2p |
|---|---|---|
| 5/5 | .03125 | .0625 |
| 6/6 | .01563 | .0313 |
| 7/7 | .00782 | .0157 |
| 7/8 | .03516 | .0732 |
| 8/9 | .01954 | .0391 |

Figure 14:
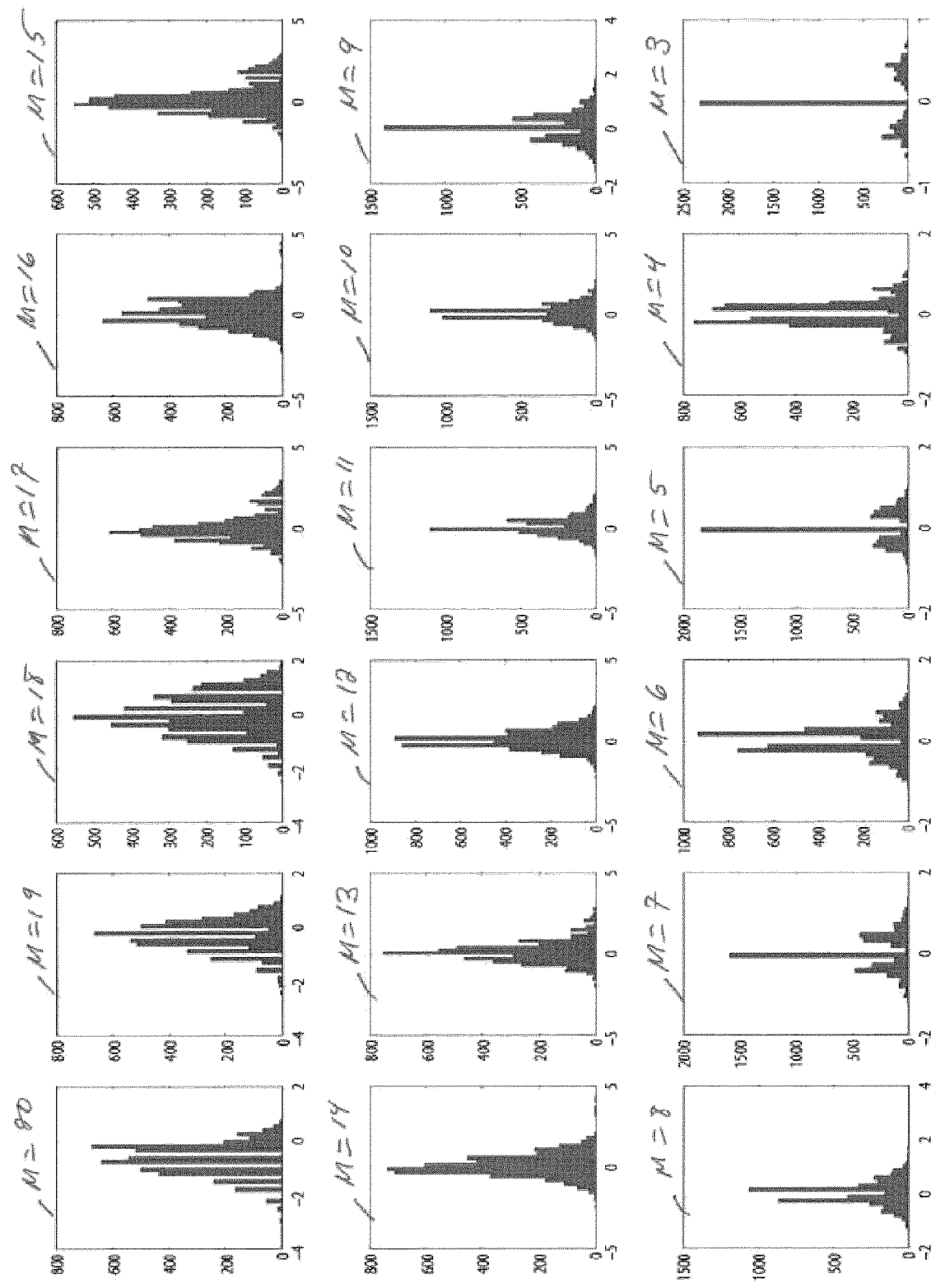
FIG. 14 is a series of graphs showing differences in speed over a plurality of trials.

Using the difference in speed is not feasible because the distributions at small and medium sample sizes are not well approximated by standard distributions, making the detection of outliers difficult. FIG. 14 is a series of graphs showing differences in speed over a plurality of trials. In FIG. 14, speed differences over 18 of the last 20 trials, shown for values of M from 20 to 3. When testing the difference between nearby trials, the distribution follows one of two patterns: (1) when speed threshold changes an odd number of times, there is a peak at 0 and a distribution on either side, and (2) when speed threshold changes an even number of times, there are two distributions on either side. As the difference is computed over more trials (12 and above), the distribution approaches the normal distribution.

Those of ordinary skill in the art will realize that the description of the system and method for determining a perceptual-cognitive signature of a subject is illustrative only and is not intended to be in any way limiting. Other embodiments will readily suggest themselves to such persons with ordinary skill in the art having the benefit of the present disclosure. Furthermore, the disclosed system and method may be customized to offer valuable solutions to existing needs and problems of optimally setting parameters according to a subject's perceptual-cognitive training needs.

In the interest of clarity, not all of the routine features of the implementations of the system and method are shown and described. It will, of course, be appreciated that in the development of any such actual implementation of the system and method, numerous implementation-specific decisions may need to be made in order to achieve the developer's specific goals, such as compliance with application-, system-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of perceptual-cognitive abilities of subjects having the benefit of the present disclosure.

In accordance with the present disclosure, the components, process operations, and/or data structures described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of operations is implemented by a computer or a machine and those operations may be stored as a series of instructions readable by the machine, they may be stored on a tangible medium.

Systems and modules described herein may comprise software, firmware, hardware, or any combination(s) of software, firmware, or hardware suitable for the purposes described herein. Software and other modules may reside on servers, workstations, personal computers, computerized tablets, personal digital assistants (PDA), and other devices suitable for the purposes described herein. Software and other modules may be accessible via local memory, via a network, via a browser or other application or via other means suitable for the purposes described herein. Data structures described herein may comprise computer files, variables, programming arrays, programming structures, or any electronic information storage schemes or methods, or any combinations thereof, suitable for the purposes described herein.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. A system for determining a perceptual-cognitive signature of a subject, comprising:
a display of a plurality of objects;
an interface adapted to receive, from the subject, identifications of one or more target objects amongst the plurality of objects; and
a controller configured to:
specify a number of target objects;
set a speed of the plurality of objects moving on the display for a predetermined duration in each of a series of core trials, and
determine the perceptual-cognitive signature of the subject according to:
the number of target objects,
the predetermined duration of each of the series of core trials, and
a correctness of the identifications, by the subject after each predetermined duration, of the one or more target objects over the series of core trials,
wherein the series of core trials
comprises a selective attention test series, a sustained attention test series and a stamina attention test series, wherein the selective test series is followed by the sustained attention test series and the sustained attention test series is followed by the stamina attention test series.

2. The system of claim 1, wherein the perceptual-cognitive signature of the subject defines a level of attentional capabilities of the subject.

3. The system of claim 1, wherein a core trial is defined by:
a presentation of the plurality of objects positioned on the display;
a visual identification of the objects;
a removal of the visual identification of the target objects;
a movement of the plurality of objects on the display for the predetermined duration;
a reception of the identifications of the objects;
a provision of feedback to the subject of the correctness of the identifications of the objects; and
an increase or decrease of the speed of the plurality of objects according to the correctness of the identifications of the one or more target objects.

4. The system of claim 1, wherein the controller is further configured to:
initiate the series of core trials with a given core trial having a given number of target objects, the objects moving at a given speed in the given core trial;
increase the given speed of the objects over a course of the series of core trials if the identifications of the one or more target objects are correct;
increase a subsequent number of target objects beyond the given number of target objects for a subsequent series of core trials if the given speed of the series of core trials reaches a pass speed threshold; and
bypass the subsequent series of core trials if the given speed of the given core trial fails to reach the pass speed threshold.

5. The system of claim 4, wherein a final number of target objects in a final series of core trials is four.

6. The system of claim 1, wherein the controller is further configured to:
set a speed of the plurality of objects for the sustained attention test series according to a speed of the plurality of objects of the selective test series in which the speed reached a success speed threshold greater than a pass speed threshold;
set a number of the target objects for the sustained attention test series according to a number of the target objects of the selective test series;
execute a predetermined number of repetitions with the speed of the plurality of objects and the number of the target objects set for the sustained attention test series, a duration of a next repetition being increased if a previous repetition provides correct identifications of the number target objects, the duration of the next repetition being decreased if the previous repetition provides incorrect identifications of the number of target objects; and
calculate an average of 5 last repetition durations.

7. The system of claim 6, wherein the predetermined number of repetitions is 50.

8. The system of claim 1, wherein the controller is further configured to:
determine a core trial baseline according to a speed of the plurality of objects and a number of the target objects in 3 core trials in which the identifications of the one or more target objects are correct;
use the core trial baseline for the stamina attention test series; and
end the stamina attention test series when an end criterion is met, the end criterion being defined as a number of failed trials within a number of last successive trials.

9. The system of claim 8, wherein the end criterion is defined as the subject failing 3 out of 3, 4 out of 4, 5 out of 5, 5 out of 6, 5 out of 7, or 7 out of 8 last successive trials.

10. The system of claim 1, comprising:
- an input interface operatively connected to the controller and adapted to receive parameters of the series of core trials; and
- an output interface operatively connected to the controller and adapted to output the perceptual-cognitive signature of the subject.

11. The system of claim 1, comprising a three dimensional display.

12. The system of claim 1, comprising a full immersive virtual environment.

13. The system of claim 1, comprising a head-mounted display.

\* \* \* \* \*